United States Patent [19]

Nöth et al.

[11] Patent Number: 4,731,463

[45] Date of Patent: Mar. 15, 1988

[54] PROCESS OF HYDROBORONIZING ALKENES AND ALKYNES

[75] Inventors: Heinrich Nöth, Grünwald; Detlef Männig, Munich, both of Fed. Rep. of Germany

[73] Assignee: Metallgesellschaft Aktiengesellschaft, Frankfurt am Main, Fed. Rep. of Germany

[21] Appl. No.: 894,292

[22] Filed: Aug. 7, 1986

[30] Foreign Application Priority Data

Aug. 7, 1985 [DE] Fed. Rep. of Germany ....... 3528320

[51] Int. Cl.$^4$ ............................................. C07C 107/02
[52] U.S. Cl. ..................................... 558/288; 558/291
[58] Field of Search ................................ 558/288, 291

[56] References Cited

U.S. PATENT DOCUMENTS 3,445,426   5/1969   Lee ................................ 558/288 X
4,611,013   9/1976   Ashida ........................... 558/290 X
4,629,578  12/1986   Liston ............................ 558/291 X

OTHER PUBLICATIONS

Brown et al., Jacs 97(18) 5249–5255 (1975).
Chemical Abstracts 92 139884s (1980).
Journal of the American Chemical Society, 97:18, dated 3 Sep. 1975, Brown, Gupta 1,3,2-Benzodioxaborole, A New Hydroboration Reagent.
Inorganic Syntheses, 10, pp. 67–71 (1967).

*Primary Examiner*—Paul F. Shaver
*Attorney, Agent, or Firm*—Karl F. Ross; Herbert Dubno

[57] ABSTRACT

In a process for hydroboronizing alkenes or alkynes with catecholborane (1,3,2-benzodioxaborolane) optionally in the presence of an added organic solvent the reaction is catalyzed by a complex compound having one of the formulas:

(I) $RhCl(CO)_x[E(C_6H_5)_3]_{3-x}$, wherein "E" is arsenic or phosphorous and "x" equals 0 or 1,
(II) $[RhCl(alkene)_2]_2$,
(III) $[(C_6H_5)_3P]_3Ru(CO)ClH$ or
(IV) $[(C_6H_5)_3P]_3RuCl_2$, particularly suitable catalysts are, e.g. tris(triphenylphosphine)rhodium(I) chloride and bis(cyclooctadiene)rhodium(I) chloride.

7 Claims, No Drawings

PROCESS OF HYDROBORONIZING ALKENES AND ALKYNES

CROSS REFERENCE TO RELATED APPLICATION

This application is related to the commonly assigned copending application Ser. No. 894,329 filed 7 Aug. 1986.

FIELD OF THE INVENTION

Our present invention relates to a process of hydroboronizing alkenes and alkynes with catecholborane.

BACKGROUND OF THE INVENTION

It is known (see J.A.C.S. 97, P. 5249 (1975)) that catecholborane (1,3,2-benzo-dioxaborolan) can be used to reduce alkenes and alkynes, usually in the absence of a solvent and at an elevated temperature, with an almost quantitative yield.

For this purpose, the catecholborane is used in a stoichiometric excess and the reaction is carried out at temperatures between about 70° and 120° C.

It is also known (see Inorg. Snyth. 10, PP. 67–71 (1967))) that the solutions of the complex compound tris(triphenylphosphine)rhodium(I) chloride will reversibly absorb molecular hydrogen at a temperature of 25° C. and a pressure of 1 kg/cm$^2$. Such solutions are highly effective catalysts for the homogenous hydrogenation of alkenes and alkynes.

The known processes of hydroboronizing alkenes and alkynes are not satisfactory in all cases because catecholborane is used at elevated temperatures and in a substantial surplus. In particular, those processes will fail if the organic substrate contains functional groups, particularly keto groups, which will be reduced more quickly than the C=C function.

OBJECTS OF THE INVENTION

It is an object of the invention to provide an improved process for the selective hydroboronization of alkenes and alkynes in which the disadvantage of the known process, particularly the disadvantages mentioned hereinbefore, are avoided. In connection with the invention, the term alkenes covers monoolefins, diolefins and cycloolefins as well as other olefinic compounds, such as unsaturated ketones and nitriles.

DESCRIPTION OF THE INVENTION

This object is accomplished in accordance with the invention by the provision of a process in which alkenes or alkynes are hydroboronized with 1,3,2-benzodioxaborolane (catecholborane) optionally in the presence of an added organic solvent. In the process of the invention the reaction is catalyzed by a complex compound selected from the group which consists of:

(I) $RhCl(CO)_x[E(C_6H_5)_3]_{3-x'}$
wherein "E" is arsenic or phosphorous and "x" equals 0 or 1,
(II) $[RhCl(alkene)_2]_{2'}$
(III) $[(C_6H_5)_3P]_3Ru(CO)ClH$ and
(IV) $[C_6H_5)_3P]_3RuCl_2$ In the process in accordance with the invention, a hydroboronizing system is prepared which has a selective activity and a long shelf life and permits the reaction to be carried out at a high rate. That system can easily be handled and effectively be proportioned.

Examples of suitable rhodium(I) chloride complex compounds are:
Tris(triphenylphosphine)rhodium(I) chloride $[P(C_6H_5)_3]_3RhCl$,
Tris(diphenylphosphine)rhodium(I) chloride $[(C_6H_5)_2P]_3RhCl$,
Bis(triphenylphosphine)rhodium(I) carbonylchloride $[P(C_6H_5)_3]_2(CO)RhCl$,
Bis(triphenylarsine)rhodium(I) carbonylchloride $[As(C_6H_5)_3]_2(CO)RhCl$,
Bis(ethylene)rhodium(I) chloride $[(C_2H_4)_2RhCl]_2$
Bis(cyclooctadiene)rhodium(I) chloride $[(COD)_2RhCl]_2$.

Suitable ruthenium (II) chloride complex compounds are:
Tris(triphenylphosphine)carbonylruthenium(II) chloride hydride $[(C_6H_5)_3P]_3Ru(CO)ClH$
Tris(triphenylphosphine)ruthenium(II) dichloride $[(C_6H_5)_3P]_3RuCl_2$.

The catalytic hydroboronization may be assumed to proceed approximately in accordance with the following reaction scheme, in which "L" designates the residue $P(C_6H_5)_3$:

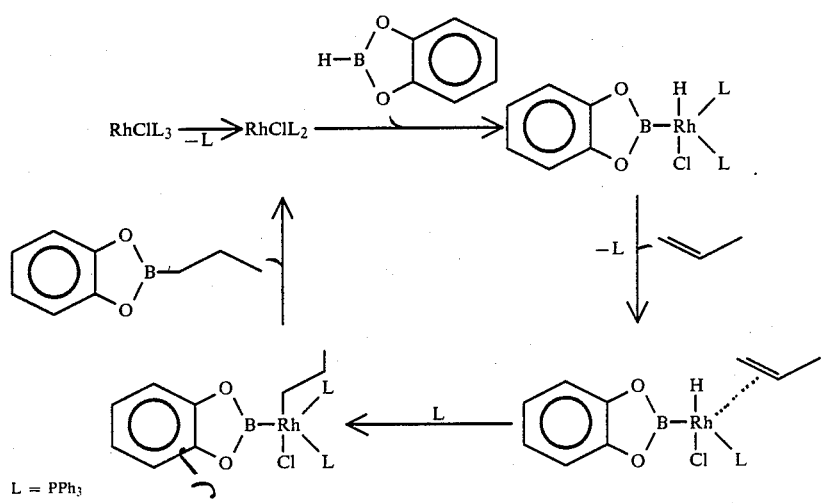

In the process in accordance with the invention the olefin, which may consist of unsaturated ketones or nitriles, or the alkaline, and the catalyst such as tris(triphenylphosphine)rhodium(I) chloride, are dispersed in a solvent, such as benzene, toluene, hexane, or in a slightly coordinating ether, such as diethylether, and catecholborane is added with stirring.

The reaction is effected at room temperature, generally at temperatures of 15° to 25° C. Lower temperatures (e.g. 0° C.), or higher temperatures (e.g. 40° C.) may also be used but their use will not afford appreciable advantages regarding the yield and reaction rate.

When the hydroboronization has been initiated, the color of the reaction mixture changes from red to yellow. The color returns to red when the reaction has been completed. When the reaction has been terminated, the reaction mixture is heated, optionally under a negative pressure, to a temperature above the boiling point of the alkene or alkyne, e.g. to a temperature of 70° C., so that surplus alkene or alkyne will be driven off. In many cases the catalyst or its catalytically active derivative is only slightly soluble in the reaction medium and can be separated by filtration from the hydroboronized product that is in solution. The catalyst or its derivative may optionally be washed, e.g. with toluene, and be reused.

The hydroboronized product may then be transformed to various derivatives of the alkene or alkyne in known manner by suitable reactions, protonolysis, oxidation, amination, carbonylation and halogenolysis (see H. C. Brown "*Organic Synthesis via Boranes*", J. Wiley. Intersc. Publ., New York 1975).

The catalyst and the catecholborane are produced by processes known per se. However, preferably the catecholborane is produced by the process described in the above-identified application.

To produce the catalyst, such as tris(triphenylphosphine)rhodium(I) chloride, rhodium trichloride trihydrate in ethanol and triphenylphosphine dissolved in hot ethanol are reacted under reflux and under a nitrogen atmosphere. The resulting crystalline product has a dark-red color and is filtered off (J. A. Osborn, G. Wilkinson in "Inorg. Synth.", 10 (1967), page 67).

Catecholborane (1,3,2-benzodioxaborolane) can easily be produced by a reaction of catechol with borane in tetrahydrofurane under a nitrogen atmosphere at temperatures of about 0° C. The reaction product is distilled from the solution under a reduced pressure.

In a particularly desirable process, catecholborane is produced by a reaction of tris(catecholate)bisborane with alkali metal-boron hydride in diethyl ether with an activating grinding operation and with an optional co-use of lithium halide as a solubilizer. A solvent-free product can be obtained in that process as described in the aforementioned copending application.

The advantage afforded by the process in accordance with the invention is that alkenes and alkynes, which are highly volatile and thermally unstable, can be hydroboronized at relatively low temperatures. The process in accordance with the invention can be used to hydroboronize also the C=C double bond of unsaturated ketones or nitriles substantially without an adverse action on the carbonyl or nitrile function. Without a catalyst, the keto group or nitrile group will be quantitatively reduced.

SPECIFIC EXAMPLES

The invention will be illustrated in greater details in the following Examples:

(A) Catalytic Hydroboronization of Olefins

In a three-necked 50 ml flask provided with a magnetic stirrer, a dropping funnel, a thermometer, a reflux condenser and a nitrogen inlet port, the olefin (45 millimoles) was dissolved in 7.5 ml benzene and 20.8 mg (0.05 mole percent) [(C$_6$H$_5$)$_3$P]$_3$RhCl were added. Catecholborane was added in a stoichiometrically equivalent quantity to the red solution being stirred during a period of 10 to 20 minutes. The reduction is exothermic and may result in a boiling of the benzene. After 25 minutes, a distillative separation was effected, by which the 2-organyl-benzo-1,3,2-dioxaborolane is isolated.

The results of that reaction performed with a number of olefins are compiled in the following table. The yield has not been optimized.

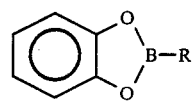

| Substrate | Yield % | B.p., °C./torr | δ$^{11}$B (ppm) |
|---|---|---|---|
| 1-octene | 77.7 | 96–97/0.12 | 35.8 |
| Norbornene | 77.8 | 94/0.01 | 35.5 |
| Cyclopentene | 83.3 | 62/0.01 | 36.9 |
| Cyclohexene | 21.5$^a$ | 71/0.01 | 35.4 |
| 2,4,4-trimethyl-1-pentene | 5.8$^b$ | 96/0.08 | 35.4 |
| 3-vinyl-cyclohexene | 50.0$^c$ | 83/0.1 | 35.7 |

$^a$50% conversion after 4 days
$^b$About 50% conversion after 2 days
$^c$Reaction only at the vinyl group Similar results, after longer reaction times, are obtained with ruthenium(II) chloride complex compounds, such as [(C$_6$H$_5$)P]$_3$Ru(CO)ClH or [(C$_6$H$_5$)$_3$P]$_3$RuCl$_2$.

(B) Catalytic Hydroboronization of Unsaturated Ketones

The procedure is the same as that described in (A). The reactants are used in the following quantities: 22.5 millimoles of the substrate and of the catecholborane, 0.05 mole percent tris(triphenylphosphine)rhodium(I) chloride and 70 ml benzene. The reaction mixture was stirred for 1 to 2 hours and was then separated by distillation.

| Substrate | Catalyst | B—R$^a$ | B—OR$^a$ | Yield %$^b$ | B.p., °C./torr | δ$^{11}$B ppm |
|---|---|---|---|---|---|---|
| (CH$_2$=CHCH$_2$CH$_2$C(O)CH$_3$) | − | 0 | 100 | 75.8 | 74/0.08$^c$ | 23.2$^c$ |
| | + | 83 | 17 | 53.8 | 102/0.09$^d$ | 35.7$^d$ |

-continued

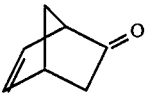

| Substrate | Catalyst | | Yield %[b] | B.p., °C./torr | $\delta^{11}B$ ppm |
|---|---|---|---|---|---|
| 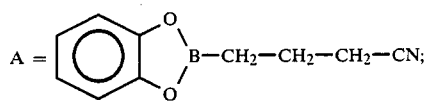 | — | 0:100 | 92.0 | 96–97/0.1[c] | 23.3[c] |
| | + | 83:17 | 76.7 | 124/0.02[d] | 35.5[d] |

[a] $^{11}B$ conversion ratio determined by NMR spectroscopy
[b] Related to isolated product
[c] Stated for BO₃ product
[d] Stated for CBO₂ product (C) Catalytic Hydroboronization of a Nitrile A solution of 5.0 ml catecholborane (45 millimoles) in 10 ml benzene was added in drops and with cooling with ice to a solution of 3.62 ml allyl cyanide (45 millimoles) and 208 kg tris(triphenylphosphine)rhodium(I) chloride in 20 ml benzene. After 5 hours, an almost complete conversion was revealed by a $^{11}$BNMR spectrum of the solution. The ratio of the CBO₂ product to the NBO₂ product amounted to 88:12. The solvent was withdrawn after 6 hours and was then distilled in a vacuum. The yield of the hydroboronized product A+B having a C=C double bond amounted to 4.05 g (48.1%). That product had a boiling point of 102° C. at 0.07 torr.

$\delta^1H$ (CDCl₃) 7.2–6.9 m (8H); 2.6–2.2m (4H); 2.0–1.7 m (3H); 1.4–1.2 m (5H)

$\delta^{13}C$(CDCl₃) 147.3; 122.0; 118.9; 19.3; 14.04; 9.1 (br) about 60%, 147.2; 122.2; 118.6; 118.8; 19.2; 18.2; 9.1 (br) about 40%

$\delta^{11}B$ (CDCl₃) 34.9 h ½=670 Hz

When the same reaction is carried out without a catalyst, an $^{11}B$ NMR spectrum of the solution indicates a conversion of about 40% after 4 hours. That conversion results only in the reduction of the nitrile group ($\delta^{11}B$ 23.1 ppm). After a prolonged stirring, a white substance is gradually separated, which cannot be dissolved or distilled.

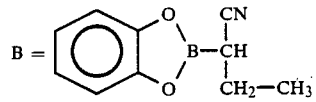

(D) Catalytic Hydroboronization of Alkynes

A solution of 3.7 g (45 millimoles) 1-hexyne in 5 ml benzene was dropped into a mixture of 5.4 g (45 millimoles) catecholborane and 20.8 mg (0.05 millimoles) ClRh(PPh₃)₃ in 2.5 ml benzene while the mixture was stirred. After 25 minutes, a distillative separation resulted in a recovery of 4.73 g (52%) hexene-2-yl-1,3,2-benzodioxaborolane, boiling point 79°–60° C. at 0.01 torr, $\delta^{11}B$ 31.1 ppm, $\delta^{1H}$ 7.15–6.82 (5H); 5.74 (1H); 2.3–1.6 (2H); 1.5–1.0 (4H); 1.0–0.7 (3H).

3-hexene-3-yl-1,3,2-benzodioxaborolane was hydroboronizd in the same manner. Yield 2.82 g (31%); boiling point 71°–72° C. at 0.01 torr; $\delta^{11}B$ 32.0 ppm; $\delta^1H$: 7.15–6.75 (5H); 2.7–1.7 (4H); 1.3–0.8 (6H).

We claim:

1. A process for hydroboronizing an alkene or alkyne which comprises reacting at a temperature of 0° to 40° C. the alkene or alkyne with catecholborane in an organic solvent selected from the group which consists of benzene, toluene, hexane, and slightly coordinating ethers, in the presence of a complex catalytically effective compound selected from the group consisting of:
   (I) RhCl(CO)ₓ[E(C₆H₅)₃]₃₋ₓ wherein E is arsenic or phosphorous and x is 0 or 1,
   (II) [RhCl(alkene)₂]₂,
   (III) [(C₆H₅)₃P]₃Ru(CO)ClH, and
   (IV) [(C₆H₅)₃P]₃RuCl₂.

2. The process defined in claim 1, wherein tris(triphenylphosphine)rhodium(I) chloride is used as a catalyst.

3. The process defined in claim 1 wherein bis(triphenylphosphine)rhodium(I) carbonylchloride is used as a catalyst.

4. The process defined in claim 1 wherein bis(triphenylarsine)rhodium(I) carbonylchloride is used as a catalyst.

5. The process defined in claim 1 wherein bis(ethylene)rhodium(I) chloride is used as a catalyst.

6. The process defined in claim 1 wherein bis(cyclooctadiene)rhodium(I) chloride is used as a catalyst.

7. The process as defined in claim 1 wherein the temperature is 15° to 25° C.

* * * * *